US007442764B2

(12) United States Patent
Rozema et al.

(10) Patent No.: US 7,442,764 B2
(45) Date of Patent: *Oct. 28, 2008

(54) REVERSIBLE MODIFICATION OF AMINE-CONTAINING COMPOUNDS

(75) Inventors: David B. Rozema, Madison, WI (US); Darren Wakefield, Madison, WI (US); Jon A. Wolff, Madison, WI (US); Kirk Ekena, Madison, WI (US); James E. Hagstrom, Middleton, WI (US)

(73) Assignee: Mirns Bio Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/312,319

(22) Filed: Dec. 20, 2005

(65) Prior Publication Data

US 2006/0122096 A1 Jun. 8, 2006

Related U.S. Application Data

(63) Continuation-in-part of application No. 11/046,590, filed on Jan. 28, 2005, now Pat. No. 7,098,032, and a continuation-in-part of application No. 10/444,662, filed on May 23, 2003, now Pat. No. 7,019,113, and a continuation-in-part of application No. 09/589,978, filed on Jun. 7, 2000, now Pat. No. 6,630,351, said application No. 11/046,590 is a continuation of application No. 10/095,680, filed on Mar. 11, 2002, now Pat. No. 6,919,091.

(60) Provisional application No. 60/383,298, filed on May 24, 2002, provisional application No. 60/137,859, filed on Jun. 7, 1999, provisional application No. 60/172,809, filed on Dec. 21, 1999, provisional application No. 60/167,836, filed on Nov. 29, 1999.

(51) Int. Cl.
*C07K 1/107* (2006.01)
*A61K 38/00* (2006.01)
*C07K 2/00* (2006.01)

(52) U.S. Cl. ........................... 530/345; 530/300; 514/2

(58) Field of Classification Search ....................... None
See application file for complete search history.

(56) References Cited

U.S. PATENT DOCUMENTS

| | | | | |
|---|---|---|---|---|
| 4,179,337 | A * | 12/1979 | Davis et al. | 435/181 |
| 6,590,071 | B1 * | 7/2003 | Shen et al. | 530/300 |
| 6,630,351 | B1 * | 10/2003 | Monahan et al. | 435/455 |
| 7,019,113 | B2 * | 3/2006 | Rozema et al. | 530/333 |
| 7,138,382 | B2 * | 11/2006 | Wolff et al. | 514/44 |

FOREIGN PATENT DOCUMENTS

WO WO 0034236 A1 * 6/2000

OTHER PUBLICATIONS

Asayama S et al. "Synthesis of novel polyampholyte comb-type copolymers consisting of a poly(L-lysine) backbone and hyaluronic acid side chains for a DNA carrier." Bioconjug Chem. 1998; vol. 9 No. 4 pp. 476-481.

Blattler WA et al. "New heterobifunctional protein crosslinking reagent that forms an acid-labile link." Biochemistry 1985 vol. 24 No. 6 pp. 1517-1524.

Boussif O et al. "A versatile vector for gene and oligonucleotide transfer into cells in culture and in vivo: polyethylenimine," Proc Natl Acad Sci USA; 1995 vol. 92 pp. 7297-7301.

Curiel DT et al. "Adenovirus Enhancement of Transferrin-Polylysine-Mediated Gene Delivery." Proc Natl Acad Sci USA 1991, vol. 88, p. 8850-8854.

Danko et al. "High expression of naked plasmid DNA in muscles of young rodents." Hum. Mol. Genetics 1997 vol. 6 pp. 1435.

Dash PR et al. "Factors affecting blood clearance and in vivo distribution of polyelectrolyte complexes for gene delivery" Gene Ther; 1999 vol. 6 No. 4 pp. 643-650.

Dixon HBF et al. "Reversible Blocking of Amino Groups with Citraconic Anhydride." Biochemical Journal. 1968. 109:312-313.

Felgner PL et al. "Lipofection: A Highly Efficient, Lipid-Mediated DNA-Transfection Procedure." Proc Natl Acad Sci USA, 1987, vol. 84, p. 7413-7417.

Futaki S. "Arginine-rich peptides: potential for intracellular delivery of macromolecules and the mystery of the translocation mechanisms." Int J Pharm. 2002. 245(1-2):1-7.

Garman AJ et al. "The Preparation and Properties of Novel Reversible Polymer-Protein Conjugates." FEBS Letters. 1987. 223(2):364-365.

Greenwald RB et al. "Poly(ethylene glycol) Conjugated Drugs and Prodrugs: A Comprehensive Review." Critical Reviews in Therapeutic Drug Carrier Systems 2000. 17:101-161.

Hawley-Nelson P et al. "LipofectAMINE Reagent: A New, higher efficiency polycationic liposome transfection reagent." Focus Vo. 15, No. 3, p. 73-79.

Kamata H et al. "Amphiphilic peptides enhance the efficiency of liposome-mediated DNA transfection." Nucleic Acids Res. 1994 vol. 22 No. 3 pp. 536-537.

Kirby AJ "Effective Molarities For Intramolecular Reactions." Effective Molarities; p. 184-279.

Kirby AJ et al. "Structure and Efficiency in Intramolecular and Enzymic Catalysis. Catalysis of Amide Hydrolysis by the Carboxy-group of Substituted Maleamic Acids." J Chem Soc Perkin 1972. vol. 11, p. 1206-1214.

Kishore K et al. "Polymers Containing Disulfide, Tetrasulfide, Diselenide and Ditelluride Linkages in the Main Chain." Advances in Polymer Sciences; 1995, vol. 121, p. 83-92.

(Continued)

*Primary Examiner*—Andrew D Kosar
(74) *Attorney, Agent, or Firm*—Kirk Ekena; Mark K. Johnson

(57) ABSTRACT

An process for the reversible modification of an amine-containing compound is described. Modification of the compound can be used to facilitate delivery of molecules to cells in vitro and in vivo or to alter interactions or activities the compounds. The described modifiers can also be utilized as cross-linkers.

20 Claims, 4 Drawing Sheets

OTHER PUBLICATIONS

Kratz F et al. "Drug-polymer conjugates containing acid-cleavable bonds." Critical Reviews in Therapeutic Drug Carrier Systems, 1999 vol. 16 No. 3 p. 245-288.
Kresge AJ et al. "Vinyl Ether Hydrolysis. 9. Isotope Effects on Proton Transfer From the Hydromium Ion." Journal of American Chemical Society, 1977, p. 7228-7233.
Lee HJ et al. "Pharmacokinetics and delivery of tat and tat-protein conjugates to tissues in vivo." Bioconjug Chem 2001 vol. 12 pp. 995-999.
Legendre JY, et al. "Delivery of plasmid DNA into mammalian cell lines using pH-sensitive liposomes: Comparison with cationic liposomes." Pharmaceut. Res. 1992 vol. 9 pp. 1235-1242.
Lindgren M et al. "Cell-penetrating peptides." Trends Pharmacol Sci 2000. vol. 21 p. 99-103.
Madsen F et al. "Complexation Graft Copolymer Networks: Swelling Properties, Calcium Binding and Proteolytic Enzyme Inhibition." Biomaterials, 1999, vol. 20, p. 1701-1708.
Mechtler K et al "Gene transfer mediated by influenze virus peptides: the role of peptide sequences" New J. Chem. 1997 vol. 21 pp. 105-111.
Meyer O et al. "Copolymers of N-isopropylacrylamide can trigger pH sensitivity to stable liposomes." FEBS Letters; 1998 vol. 421 pp. 61-64.
Mukherjee S et al. "Endocytosis." Physiological Reviews, 1997, vol. 77, No. 3, p. 759-803.
Murthy N et al. "The design and synthesis of polymers for eukaryotic membrane disruption." J Control Release 1999 vol. 61 pp. 137-143.
Naganawa A et al. "Synthetic Studies on Tautomycin Synthesis of 2,3-Disubstituted Maleic-Anhydride Segment." Tetrahedron; 1994 vol. 50 No. 30 pp. 8969-8982.
Netz RR, Joanny JF. "Complexation Behavior of Polyampholytes and Charged Objects." Macromolecules. 1998; vol. 31 No. 15 p. 5123-5141.
Nieto MA et al. "Effects of Temperature and pH on the Regeneration of the Amino Groups of Ovalbumin After Modification with Citraconic and Dimethylmaleic Anhydrides." Biochimica et Biophysica Acta. 1983. 749:204-210.
Nishikubo T et al. "Degradation of Dehydrochlorinated Poly(epichlorohydrin) Using Photo-Generated Cationic Catalysts." Journal of Polymer Science, 1986, vol. 24, p. 1097-1108.
O'Brien-Simpson NM et al. "Polymerization of Unprotected Synthetic Peptides: A View Toward Synthetic Peptide Vaccines." J. Am. Chem. Soc. 1997 vol. 119, p. 1183-1188.
Ogris M et al. "PEGylated DNA/transferrin-PEI complexes: reduced interaction with blood components, extended circulation in blood and potential for systemic gene delivery," Gene Ther; 1999 vol. 6(4) pp. 595-605.
Ohmori N et al. "The enhancing effect of anionic alpha-helical peptide on cationic peptide-mediating transfection systems." Biochem Biophys Res Commun. 1997 vol. 235 No. 3 pp. 726-729.
Pastan I et al. "Pseudomonas exotoxin: chimeric toxins." J Biol Chem. 1989 vol. 264 No. 26 pp. 15157-15160.
Perez M et al. "Comonomer Sequence Assignment of the 13C n.m.r. Spectra of Some Poly (epichlorohydrin) Derivatives Obtained by Nucleophilic Substitution." Polymer, 1998 vol. 39, No. 17, p. 3885-3892.
Plank et al. "Activation of the complement system by synthetic DNA complexes: a potential barrier for intravenous gene delivery," Hum Gene Ther; 1996 vol. 7(12) pp. 1437-1446.
Reddy JA et al. "Enhanced folate receptor mediated gene therapy using a novel pH-sensitive lipid formulation." J of Controlled Release; 2000 vol. 64 No. 1-3 pp. 27-37.
Remy JS et al. "Gene Transfer With a Series of Lipophilic DNA-Binding Molecules." Bioconjugate Chem. 1994 vol. 5, pp. 647-654.
Ross PC et al. "Lipoplex size is a major determinant of in vitro lipofection efficiency." Gene Therapy 1999 vol. 6 No. pp. 651-659.
Schwarze SR et al. "In vivo protein transduction: delivery of a biologically active protein into the mouse." Science 1999. 285:1569-1572.
Seetharam S et al. "Increased Cytotoxic Activity of Pseudomonas Exotoxin and Two Chimeric Toxins Ending in KDEL*." The Journal of Biological Chemistry, 1991, vol. 266, No. 26 p. 17376-17381.
Senior JH et al. "Interaction of Positively-Charged Liposomes with Blood: Implications for Their Application In Vivo." Biochemica et Biophysica Acta 1991 vol. 1070, No. 1 p. 173-179.
Sezaki H et al. "Soluble macromolecular carriers for the delivery of antitumour drugs." Adv Drug Deliv Rev 1989 vol. 3 No. 2 pp. 247-266.
Shah D et al. "Transcellular delivery of an insulin-transferrin conjugate in enterocyte-like Caco-2 cells." J Pham Sci. 1996. vol. 85 No. 12 p. 1306-1311.
Sitaram N et al. "Interaction of Antimicrobial Peptides with Biological and Model Membranes: Structural and Charge Requirements for Activity." Biochimica et Biophysica Acta 1999 vol. 1462 p. 29-54.
Thorpe PE et al. "Comparison of Two Anti-Thy 1.1-Abrin A-Chain Immunotoxins Prepared With Different Cross-Linking Agents: Antitumor Effects, In Vivo Fate, and Tumor Cell Mutants." JNCI. 1987 vol. 79, No. 5, pp. 1101-1111.
Trubetskoy VS et al. "Caged DNA Does Not Aggregate in High Ionic Strength Solutions," Bioconjugate Chem; 1999 vol. 10 No. 4 pp. 624-628.
Trubetskoy VS et al. "Layer-by-layer deposition of oppositely charged polyelectrolytes on the surface of condensed DNA particles," Nucleic Acids Research; 1999 vol. 27 No. 1 pp. 3090-3095.
Trubetskoy VS et al. "Self-Assembly of DNA-Polymer Complexes Using Template Polymerization." Nucleic Acids Res 1998 vol. 26 pp. 4178-4185.
Van de Wetering P et al. "Copolymers of 2-(Dimethylamino)Ethyl Methacrylate with Ethoxytriethylene Glycol Methacrylate of N-Vinyl-Pyrrolidone as Gene Transfer Agents." Journal of Controlled Release; 2000, vol. 64, p. 193-203.
Vitiello L et al. "Transfection of Cultured Myoblasts in High Serum Concentration with DODAC:DOPE Liposomes." Gene Therapy; 1998 vol. 5 No. 10 pp. 1306-1313.
Wagner E et al. "Influenza virus hemagglutinin HA-2 N-terminal fusogenic peptides augment gene transfer by transferrin-polylysine-DNA complexes: toward a synthetic virus-like gene-transfer vehicle." Proc Natl Acad Sci U S A. 1992 vol. 89 No. 17 pp. 7934-7938.
Wagner E, et al. "Delivery of drugs, proteins and genes into cells using transferrin as a ligand for receptor-mediated endocytosis." Advanced Drug Delivery Reviews 1994 vol. 14 pp. 113-135.
Wolfert MA et al. "Characterization of Vectors for Gene Therapy Formed by Self-Assembly of DNA with Synthetic Block Co-Polymers." Human Gene Therapy 1996; vol. 7 pp. 2123-2133.
Xu Y et al. "Mechanism of DNA release from cationic liposome/DNA complexes used in cell transfection," Biochemistry; 1996 vol. 35 No. 18 pp. 5616-5623.
Zauner W et al. "Rhinovirus-Mediated Endosomal Release of Transfection Complexes." Journal of Virology, 1995, vol. 69, No. 2, pp. 1085-1092.
Zhou X et al. "DNA Transfection Mediated by Cationic Liposomes Containing Lipopolylysine: Characterization and Mechanism of Action." Biochemica et Biophysica Acta 1994; vol. 1189, No. 2, pp. 195-203.
Zhou X et al. "Lipophilic Polylysines Mediate Efficient DNA Transfection in Mammalian Cells." Biochemica et Biophysica Acta; 1991 vol. 1065, pp. 8-14.

* cited by examiner

A.

B.

maleic anhydride
$R_1$ and $R_2 = H$ dimethyl maleic anhydride
$R_1$ and $R_2 = CH_3$ citraconic anhydride
$R_1$ or $R_2 = H$ and $R_2$ or $R_1 = CH_3$

*cis*-aconitic anhydride
$R_1$ or $R_2 = H$ and $R_2$ or $R_1 = CH_2CO_2H$ 2-propionic-3-methylmaleic anhydride (CDM)
$R_1$ or $R_2 = CH_3$ and $R_2$ or $R_1 = (CH_2)_2CO_2H$ CDM-thioester
$R_1$ or $R_2 = CH_3$ and $R_2$ or $R_1 = (CH_2)_2COSCH_2CO_2H$ Synthesis of CDM

SEQUENCE LISTING

```
<160> NUMBER OF SEQ ID NOS: 9

<210> SEQ ID NO 1
<211> LENGTH: 10
<212> TYPE: PRT
<213> ORGANISM: Human immunodeficiency virus

<400> SEQUENCE: 1

Gly Arg Lys Lys Arg Arg Gln Arg Arg Arg
1               5                   10


<210> SEQ ID NO 2
<211> LENGTH: 16
<212> TYPE: PRT
<213> ORGANISM: Drosophila melanogaster

<400> SEQUENCE: 2

Arg Gln Ile Lys Ile Trp Phe Gln Asn Arg Arg Met Lys Trp Lys Lys
1               5                   10                  15


<210> SEQ ID NO 3
<211> LENGTH: 4
<212> TYPE: PRT
<213> ORGANISM: Homo sapiens
```

-continued

<400> SEQUENCE: 3

```
Lys Asp Glu Leu
1
```

<210> SEQ ID NO 4
<211> LENGTH: 26
<212> TYPE: PRT
<213> ORGANISM: Apis florea

<400> SEQUENCE: 4

```
Gly Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25
```

<210> SEQ ID NO 5
<211> LENGTH: 21
<212> TYPE: PRT
<213> ORGANISM: Artificial
<220> FEATURE:
<223> OTHER INFORMATION: synthetic amphipathic sequence

<400> SEQUENCE: 5

```
Lys Leu Leu Lys Leu Leu Leu Lys Leu Trp Leu Lys Leu Leu Lys Leu
1               5                   10                  15

Leu Leu Lys Leu Leu
            20
```

<210> SEQ ID NO 6
<211> LENGTH: 25
<212> TYPE: DNA
<213> ORGANISM: Photinus pyralis

<400> SEQUENCE: 6

```
cctcttacct cagttacaat ttata                                           25
```

<210> SEQ ID NO 7
<211> LENGTH: 11
<212> TYPE: PRT
<213> ORGANISM: Human immunodeficiency virus

<400> SEQUENCE: 7

```
Cys Gly Arg Lys Lys Arg Arg Gln Arg Arg Arg
1               5                   10
```

<210> SEQ ID NO 8
<211> LENGTH: 33
<212> TYPE: PRT
<213> ORGANISM: Bacteriophage T7

<400> SEQUENCE: 8

```
Lys Asn Glu Ser Ser Thr Asn Ala Thr Asn Thr Lys Gln Trp Arg Asp
1               5                   10                  15

Glu Thr Lys Gly Phe Arg Asp Glu Ala Lys Arg Phe Lys Asn Thr Ala
            20                  25                  30

Gly
```

<210> SEQ ID NO 9
<211> LENGTH: 11
<212> TYPE: PRT
<213> ORGANISM: Artificial
<220> FEATURE:
<223> OTHER INFORMATION: synthetic RGD sequence -continued

```
<400> SEQUENCE: 9

Ala Cys Asp Cys Arg Gly Asp Cys Phe Cys Gly
1               5                   10
```

REVERSIBLE MODIFICATION OF AMINE-CONTAINING COMPOUNDS

CROSS-REFERENCES TO RELATED APPLICATIONS

This application is a continuation-in-part of application Ser. No. 10/444,662, filed May 23, 2003, issued as U.S. Pat. No. 7,019,113, a continuation-in-part of application Ser. No. 09/589,978, filed Jun. 7, 2000, issued as U.S. Pat. No. 6,630,351, and a continuation-in-part of application Ser. No. 11/046,590, filed Jan. 28, 2005, issued as U.S. Pat. No. 7,098,032, application Ser. No. 10/444,662 claims the benefit of U.S. Provisional Application No. 60/383,298 filed May 24, 2002, application Ser. No. 09/589,978 claims the benefit of U.S. Provisional Applications No. 60/137,859, filed Jun. 7, 1999, No. 60/172,809, filed Dec. 21, 1999 and No. 60/167,836, filed Nov. 29, 1999, and application Ser. No. 11/046,590 is a continuation of application Ser. No. 10/095,680, filed Mar. 11, 2002, issued as U.S. Pat. No. 6,919,091.

BACKGROUND

A variety of methods and routes of administration have been developed to deliver pharmaceuticals, small molecular drugs and biologically active compounds such as peptides, hormones, proteins, and enzymes, to their site of action. Parenteral routes of administration include intravascular (intravenous, intraarterial), intramuscular, intraparenchymal, intradermal, subdermal, subcutaneous, intratumor, intraperitoneal, and intralymphatic injections that use a needle or catheter. The blood circulatory system provides systemic spread of the pharmaceutical. Polyethylene glycol and other hydrophilic polymers have been used to provide protection and to increase the circulatory time of the pharmaceutical in the blood stream by preventing interaction with blood components and preventing opsonization, phagocytosis and uptake by the reticuloendothelial system. For example, the enzyme adenosine deaminase has been covalently modified with polyethylene glycol to increase the circulatory time and persistence of this enzyme in the treatment of patients with adenosine deaminase deficiency. The controlled release of pharmaceuticals after their administration is under intensive development.

In the rational design of synthetic delivery vehicles for biologically-active compounds and macromolecules, the problem of providing for endosomal escape can be a critical barrier to efficient delivery to cytoplasmic or nuclear sites of action. Various methods have been employed in attempts overcome this barrier including: liposomes, which hypothetically fuse with cell endosomal membranes; viruses; which may either fuse with or rupture endosomal membranes; and polymer-based or other non-viral systems; which must destabilize or rupture endosomal membranes. Currently, none of these systems affects efficient escape of co-endocytosed material from internal membrane enclosed compartments. Understanding of endosomal release and ability to synthetically enhance it remain a largely unsolved process.

Both viral and synthetic processes for accomplishing endosomal release often rely upon acidification of the endosome and/or lysosome to trigger either membrane fusion or disruption. For viruses, the reduced pH of the endocytic compartment triggers a conformational change that induces endosomal escape. The pH gradient between cytoplasm and endosome also causes monoamines such as chloroquine to concentrate within endosomes thus destroying the pH gradient. The pH-sensitive amines present on polyamines such as PEI may also play a role in endosomal release although it is unclear what role protonation plays. For some liposome-based systems, pH-sensitive groups have been incorporated into lipids that enable the lipid to undergo phase transformations upon protonation. Finally, peptides and synthetic polymers containing protonatable groups have been modeled after viral sequences to become more amphipathic and membrane active in acidic environments. By limiting membrane activity to acidic vesicles, effects on the plasma membrane, and thereby cellular toxicity, are theoretically attenuated.

Unfortunately, the use of protonation to effect membrane disruption is beset with a theoretical conundrum: Endosome disruption destroys the pH-gradient (i.e. membrane integrity is essential to the maintenance of a pH gradient). With loss of a pH gradient, activity of the pH-dependent endosomalytic agent is reversed. Thus, delivery is potentially limited by the endosomal membrane resealing before macromolecules are able to diffuse out. The use of linkages that are labile within an endosomal or lysosomal milieu has previously been used in liposomes or for coupling drugs with carriers (Blattler et al. 1985). Specifically, citraconic anhydride has been used to reversibly modify the primary amine of DOPE (dioleoylphosphatidylethanolamine) (Reddy and Low 2000). However, the kinetics of reversal of this reagent are too slow to be effective in cells. Furthermore, this compound was found to be ineffective in inhibiting membrane activity of endosomalytic agents to which it was attached. In order to address the problems associated with currently available endosomalytic agents, we have developed a process of rapid irreversible activation that relies upon chemical bond cleavage to unmask a biological agent's activity.

In addition to endocytosis-dependent delivery systems, cell penetrating compounds that do not rely on endocytosis for delivery of compounds to the interior of a cell have been recently described. Delivery by these carriers involves attachment of the compound to a highly cationic, arginine-rich peptide (Lindgren et al. 2000). One such import peptide, GRKKRRQRRR (SEQ ID 1), is derived from the TAT protein of the HIV virus. This peptide, when attached to a variety of molecules facilitates their intracellular delivery both in vitro and in vivo (Schwarze et al. 1999; Lee and Pardridge 2001). Other import molecules include peptides from VP22, a herpes simplex virus protein, and the ANT protein, (RQIKIWFQNRRMKWKK, SEQ ID 2) derived from the homeo-domain of the *Drosophila* transcription factor antennapedia. These peptides contain no obvious homology other than the high content of cationic residues, especially arginine. In fact, peptides and peptide analogs composed solely of arginine residues have been shown to have import properties (Futaki 2002). For all of these peptides, import does not appear to occur via endocytosis since import occurs readily at the endocytosis impermissible temperature of 4° C. However, delivery of molecules by conjugation to these cationic import peptides is not selective. This lack of specificity results in organ distribution of TAT-modified streptavidin that is similar to the distribution of unconjugated streptavidin (Lee and Pardridge 2001). The compounds and processes we have developed for use with membrane active compounds also functions in controlling the activity of the cell penetrating compounds.

SUMMARY

In a preferred embodiment, we describe a process to modify an amine-containing molecule with a substituted maleic anhydride or derivative thereof wherein cleavage of the modification is accelerated upon exposure to pH less than 7. Upon cleavage of the modification, the amine on the molecule is regenerated. The molecule may be modified to alter interaction of the molecule with cell membranes, to attach a functional group, to link the molecule to another compound or delivery agent, to alter the activity of the molecule, or to inactivate the molecule. A preferred substituted maleic anhydride is a disubstituted maleic anhydride.

In a preferred embodiment, compounds are described that enable modification of an amine-containing molecule to reversibly alter membrane interaction of the molecule comprising: substituted maleic anhydrides having the general structure shown in FIG. 1A wherein the R to anhydride bonds can be carbon-hydrogen or carbon-carbon bonds and either $R^1$ or $R^2$, but not both, can be a hydrogen atom. A preferred substituted maleic anhydride is a disubstituted maleic anhydride wherein neither $R^1$ or $R^2$ is a hydrogen atom. We show that disubstitution increases the pH-lability of the covalent bond formed between the anhydride and an amine. A preferred disubstituted maleic anhydride is carboxy dimethylmaleic anhydride (CDM), or 2-propionic-3-methylmaleic anhydride, wherein $R^1$ is $—CH_3$ and $R^2$ is $—(CH_2)_2COOH$ or $R^2$ is $—CH_3$ and $R^1$ is $—(CH_2)_2COOH$. The addition of the carboxyl group increases the charge and water solubility of the anhydride and enhances inactivation of membrane active and cell penetrating compounds. Other functional groups may be added to either $R^1$, $R^2$, or both.

In a preferred embodiment, we describe reversible covalent crosslinkers comprising bifunctional substituted maleic anhydrides having the general structure shown in FIG. 1A wherein $R^1$ or $R^2$ contains a thioester. The thioester group enables attachment to terminal cysteines or other molecules containing a thiol separated from an amine by two to three bonds. A preferred bifunctional disubstituted maleic anhydride is carboxy dimethylmaleic anhydride thioester (CDM-thioester) wherein $R^1$ is $—CH_3$ and $R^2$ is $—(CH_2)_2COSCH_2COOH$ or $R^2$ is $—CH_3$ and $R^1$ is $—(CH_2)_2COSCH_2COOH$. The thioester-containing disubstituted maleic anhydride can be use to covalently link an amine containing molecule to a molecule containing an appropriate thiol. Attachment to the thiol occurs through native chemical ligation. The thioester itself is relatively stable when compared to activated esters such as N-hydroxysuccinimidyl esters, but will couple readily and selectively with N-terminal cysteine groups. The reaction mixture may contain other amines and other thiols, but only an appropriate thiol couples to form a stable amide with the thioester.

In a preferred embodiment, we describe a process to reversibly inactivate an amine-containing biologically active molecule wherein the molecule is modified with a substituted maleic anhydride. Efficiency of inactivation of the molecule is affected by the groups at positions $R^1$ and $R^2$ of the maleic anhydride (see FIG. 1A). Reversal of the modification regenerates the amine on the biologically active molecule, and thus activity of the molecule, and is accelerated by exposure to $pH<7$.

In a preferred embodiment, we describe a process for delivering a molecule to the interior of a cell comprising: reversibly inactivating a membrane active compound and associating the modified membrane active compound and the molecule with the cell wherein the compound and the molecule are endocytosed and the activity of the membrane active compound is restored causing disruption of the endosomal/lysosomal membrane. Reversibly inactivating the membrane active compound consists of modifying the compound by reaction with a substituted maleic anhydride. Exposure to the acidic pH environment of an endosome or lysosomes causes reactivation of the membrane active compound by cleavage of the anhydride. A preferred substituted maleic anhydride is a disubstituted maleic anhydride. A preferred maleic anhydride is CDM or CDM-thioester. The additional carboxylic acid present on CDM enhances the inactivation of certain membrane active compounds. The cell may be in vitro or in vivo.

In a preferred embodiment, we describe a process for the reversible inactivation of a cationic import molecule comprising: modifying the molecule by reaction with a substituted maleic anhydride. The reversibly inactivated import molecule can then be associated with a cell and the activity of the import molecule is restored. The reactivation of the import molecule by cleavage of the anhydride modification is enhanced in an acidic environment such as in an endosome/lysosomes or tumor region. The import molecule may be further modified by attaching other functional groups or biologically active compounds. The other groups or compounds may be attached to the import compound or to the anhydride. The modified cationic import molecule may be delivered to a cell that is in vitro or in vivo.

In a preferred embodiment, we describe a process for linking or coupling two molecules via a reversible covalent bond wherein one of the molecules contains an amine. The linkage comprises a bifunctional substituted maleic anhydride (FIG. 1A) wherein $R^1$ or $R^2$ contains a reactive group that can form a covalent or noncovalent interaction with a molecule. An example of a reactive group that forms a noncovalent interaction is biotin, which forms a stable interaction with streptavidin. An example of a reactive group that forms a covalent interaction is a thioester. The bifunctional substituted maleic anhydride may provide reversible attachment of a molecule to a biologically active compound containing an amine. Upon exposure to a reduced pH, the molecule is cleaved, regenerating the biologically active compound or pharmaceutical. The molecule may facilitate targeting or delivery of the compound, reversibly inactivate the compound, or serve another purpose. A preferred thioester-containing linker is CDM-thioester. To link two molecules with CDM-thioester, the anhydride of CDM-thioester is reacted with an anime and then the thioester is reacted with an appropriate thiol on another molecule. Alternatively, the bifunctional anhydride can be used to crosslink an amine and a thiol that are both present on the same molecule.

In a preferred embodiment, we describe a process to reversibly modify an amine by reacting the amine with a substituted maleic anhydride. Incubation at reduced pH, such as in endosome or lysosomes or regions of tumors, accelerates cleavage of the substituted maleic anhydride and regeneration of the amine. Modification of an amine can alter the chemical and physical properties of an amine-containing molecule. A preferred substituted maleic anhydride is a disubstituted maleic anhydride.

In a preferred embodiment, we describe a process for targeting the activity of a biologically active compound to the region near a tumor in vivo comprising: reversibly inactivating the compound by modification with a disubstituted maleic anhydride and injecting the modified compound into an animal. In the region of the acidic tumor, the reversal of the modification is accelerated, regenerating the active compound. If the compound contains an amine, the compound itself may be inactivated. Alternatively, the compound can be attached to a reversibly inactivated targeting molecule, such as TAT-CDM-thioester. TAT is a cell penetrating peptide. In another example, association with non-tumor cells is inhibited by modification with a disubstituted maleic anhydride such as CDM-PEG.

In a preferred embodiment, we describe a process for reversibly altering the charge of an amine comprising: modifying the amine by reacting it with a substituted maleic anhydride. The substituted maleic anhydride may contain an acidic functional group such as, but not limited to, CDM, enabling the reversible conversion of the positively charged amine to a negatively charged carboxyl. The amine can be on a polyamine. In this way, a polyamine can be partially or completely modified, allowing a wide range of charge neutralization or reversal. Regeneration of the amine by cleavage of the negatively charged anhydride modification is accelerated by exposure to pH<7.

DETAILED DESCRIPTION

We describe maleic anhydride derivatives that are usable for the reversible modification of amine-containing compounds. We further describe methods to reversibly inactivate, crosslink, or otherwise modify biologically active compounds. The described molecules and methods offer several significant advances over other methods of reversible modification. First, unlike many reversible reagents, such as disulfide containing crosslinkers, cleavage of the maleic anhydride derivatives regenerates the starting unmodified amine. Second, under mildly acidic physiological conditions, the described anhydrides are cleaved very rapidly; in only a few minutes compared to the hours or even days required for other labile bonds to be cleaved. Nevertheless, using our processes, modification of amine-containing compounds is straightforward and facile. Furthermore, reversal of the modification in vivo or in vitro is essentially unidirectional. This characteristic is especially useful when the modification is used to reversibly inhibit a membrane active compound. Once the modification is cleaved, the membrane active compound retains activity even if the local pH does not stay acidic. Conversely, many compounds which rely on protonation to become active and disrupt membranes, such as cationic lipids, are potentially inactivated if the pH rises.

Figure 1:
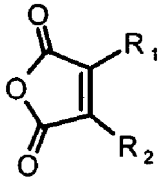
FIG. 1A-1B. Illustrations for the structures of (A) maleic anhydride derivatives and (B) succinic anhydride derivatives.
Figure 1:
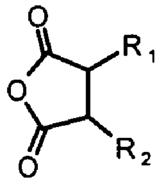
Figure 2:
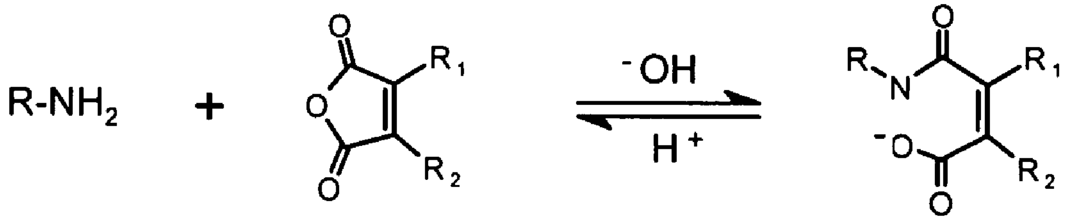
FIG. 2. Illustration of the reversible covalent bond formed between a maleic anhydride derivative and a primary amine.

Anhydrides form covalent bonds with primary amines as shown in FIG. 2 for maleic anhydride. For succinic anhydrides (FIG. 1B), the resultant covalent bond is stable and not reversible under physiological conditions. For maleic anhydrides (FIG. 1A), the resultant covalent bond can be cleaved under physiological conditions. The lability of the amide bond is directly affected by the degree of substitution at the unsaturated carbon-carbon bond of maleic anhydride (Kirby and Lancaster 1972; Nieto and Palacian 1983). The parent anhydride, maleic anhydride, has no substitution and forms the most stable maleamic acid. Citraconic and cis-aconitic-derived maleamic acids each have one substitution and are more pH-labile. Maleamic acids derived from disubstituted dimethyl maleic anhydride are the most pH-labile.

We describe maleic anhydride derivatives that add additional functionality to the anhydride reactive group. As an example, a disubstituted maleic anhydride was made in which $R^{1\ or\ 2}$ contains a thioester reactive group, thus forming a bifunctional molecule (CDM-thioester) which can be used as a coupling or crosslinking reagent. In this molecule, the $R^{1\ or\ 2}$ carboxyl group is pre-activated as a thioester. The thioester can react with an N-terminal cysteine or other thiol linked to an amine by two to three bonds to form an amide bond in a process termed native chemical ligation. The stability of the thioester allows one to react the anhydride of CDM-thioester with an amine on a compound to form maleamic acid groups without reaction between amines and the thioester. The thioester is then able to react with an N-terminal cysteine group or other appropriate thiol on a second compound.

We have developed coupling techniques using maleic anhydride derivatives to link membrane active compounds with biologically active compounds. Coupling of a membrane active compound to a biologically active compound is beneficial for delivery of certain biologically active compounds to cells, especially to cells in vivo. The process, in addition to coupling the membrane active compound to another molecule, may also reversibly inhibit the activity of the membrane active compound, thus reducing toxicity. In a similar way, it is possible to attach both a biologically active compound and a membrane active compound to a third molecule such as a polymer. Both compounds are attached through the acid-labile maleamic group of CDM-thioester. The thioesters can be coupled to a cysteine containing polymer via native chemical ligation. The same technique can be applied to attaching a biologically active compound to a targeting group or other desired compound.

Other functional groups can be envisioned that can be attached to the anhydride at either position $R^1$ or $R^2$. Any group that allows covalent or noncovalent interaction with another molecule without inhibiting coupling of the anhydride to an amine can be used.

DEFINITIONS

Functional groups include cell targeting signals, nuclear localization signals, compounds that enhance release of contents from endosomes or other intracellular vesicles (releasing signals), cell penetrating compounds, and other compounds that alter the behavior or interactions of the compound or complex to which they are attached. Functional groups may also include reactive groups, molecules that provide noncovalent interaction with another molecule or any other R group.

A cell targeting signal is any signal that enhances the association of a biologically active compound with a cell. These signals can modify a biologically active compound such as drug or nucleic acid and can direct it to a cell location (such as tissue) or location in a cell (such as the nucleus) either in culture or in a whole organism. The signal may increase binding of the compound to the cell surface and/or its association with an intracellular compartment. By modifying the cellular or tissue location of the foreign gene, the function of the biologically active compound can be enhanced. The cell targeting signal can be, but is not limited to, a protein, peptide, lipid, steroid, sugar, carbohydrate, (non-expressing) polynucleic acid or synthetic compound. Cell targeting signals such as ligands enhance cellular binding to receptors. A variety of ligands have been used to target drugs and genes to cells and to specific cellular receptors. The ligand may seek a target within the cell membrane, on the cell membrane or near a cell. Binding of ligands to receptors typically initiates endocytosis. Ligands include agents that target to the asialoglycoprotein receptor by using asialoglycoproteins or galactose residues. Other proteins such as insulin, EGF, or transferrin can be used for targeting. Peptides that include the RGD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as lipids, fatty acids, cholesterol, dansyl compounds, and amphotericin derivatives. In addition viral proteins could be used to bind cells.

After interaction of a compound or complex with the cell, other targeting groups can be used to increase the delivery of the biologically active compound to certain parts of the cell.

Nuclear localizing signals enhance the targeting of the pharmaceutical into proximity of the nucleus and/or its entry into the nucleus during interphase of the cell cycle. Such nuclear transport signals can be a protein or a peptide such as the SV40 large T antigen NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. Other NLS peptides have been derived from the hnRNP A1 protein, nucleoplasmin, c-myc, etc.

Many biologically active compounds, in particular large and/or charged compounds, are incapable of crossing biological membranes. In order for these compounds to enter the cytoplasm of a cell they must be able to cross a biological membrane. One mechanism to accomplish cytoplasmic delivery is to design the compound to possess membrane permeability. Alternatively, the biological membrane—either the cell plasma membrane or an intracellular compartment membrane where the compound is endocytosed—may be disrupted. Thirdly, the compound may be linked to a cell penetrating compound.

Compounds that are able to alter the structure of a membrane are called membrane active compounds. This change in structure can be shown by the compound inducing one or more effects on a membrane selected from the group comprising: alterations that allow small molecule permeability, pore formation, fusion and/or fission of membranes, alterations that allows large molecule permeability, dissolving or disrupting the membrane, or membrane phase transitions. This alteration can be functionally defined by the compound's activity in at least one assay selected from the group comprising: red blood cell lysis (hemolysis), liposome leakage, liposome fusion, cell fusion, cell lysis and endosomal release. An example of a membrane active agent is the bee venom peptide melittin, whose membrane activity is demonstrated by its ability to release heme from red blood cells (hemolysis).

More specifically membrane active compounds allow for transport of molecules with molecular weight greater than 50 atomic mass units to cross a membrane. This transport may be accomplished by either the total loss of membrane structure, the formation of holes (or pores) in the membrane structure, or other rearrangement or disorganization of the lipid bilayer structure. In addition, transport between liposomes or cell membranes may be accomplished by the fusion of the two membranes thus mixing of the contents of the two membranes.

These membrane active compounds, or releasing signals, enhance release of endocytosed material from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into the cytoplasm or into an organelle such as the nucleus. Releasing signals include chemicals such as chloroquine, bafilomycin or Brefeldin A1 and the ER-retaining signal (KDEL sequence, SEQ ID 3), viral components such as influenza virus hemagglutinin subunit HA-2 peptides and other types of amphipathic peptides. The control of when and where the membrane active compound is active is crucial to effective transport. If the membrane active agent is operative in a certain time and place it would facilitate the transport of the biologically active compound across the biological membrane. If the membrane active compound is too active or active at the wrong time, then no transport occurs or transport is associated with cell rupture and cell death. Nature has evolved various strategies to allow for membrane transport of biologically active compounds including membrane fusion and the use of membrane active compounds whose activity is modulated such that activity assists transport without toxicity. Many lipid-based transport formulations rely on membrane fusion and some membrane active peptides' activities are modulated by pH. In particular, viral coat proteins are often pH-sensitive, inactive at neutral or basic pH and active under the acidic conditions found in the endosome.

Membrane active peptides are membrane active compounds that are peptides. There are many naturally occurring membrane active peptides including, but not limited to: cecropin (insects), magainin (wasp), CPF 1, PGLa, Bombinin BLP-1 (all three from amphibians), seminalplasmin (bovine), indolicidin, bactenecin (both from bovine neutrophils), tachyplesin 1 (crabs), protegrin (porcine leukocytes), and defensins (from human, rabbit, bovine, fungi, and plants), gramicidin A and gramicidin S (*bacillus brevis*), the nisin (a lantibiotic from *lactococcus lactis*), androctonin (scorpion), cardiotoxin I (cobra), caerin (frog litoria splendida), and dermaseptin (frog) and the like. Viral peptides have also been shown to have membrane activity and include, but are not limited to: hemagglutinin subunit HA-2 (influenza virus), E1 (Semliki forest virus), F1 (Sendai and measles viruses), gp41 (HIV), gp32 (SIV), vp1 (Rhino, polio, and coxsackie viruses), and the like. Melittin is a highly cytotoxic and hemolytic membrane active 26-residue peptide component of bee venom (GIGAILKVLATGLPTLISWIKNKRKQ, little honey bee peptide sequence, SEQ ID 4). Multiple variations of this sequence, both naturally occurring and synthetic, also possess membrane activity. Additionally, synthetic peptides have been synthesized that have membrane activity. Synthetic peptides rich in leucines and lysines (KL or $KL_n$ motif) have been shown to have membrane activity. In particular, the peptide $H_2N$—KLLKLLLKLWLKLLKLLLKLL-$CO_2$ (SEQ ID 5), termed $KL_3$, is membrane active. There exists little to no homology or structural similarity between all the different membrane active peptides. Therefore, they are defined by their membrane activity.

Membrane active polymers are polymers that have membrane activity.

Membrane Active Amphiphiles are membrane active compounds that are amphiphilic, containing both hydrophobic and hydrophilic sections. Examples include such compounds as surfactants or detergents such as dodecylamine and dodecylsulfate.

An amphipathic compound is a molecule that contains one end that is hydrophilic while the other end is hydrophobic.

The term hydrophobic indicates in qualitative terms that the chemical moiety is water-avoiding. Hydrocarbons are hydrophobic groups. The term hydrophilic indicates in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, oligonucleotides, and groups containing amines, amides, alkoxy amides, carboxylic acids, sulfurs, or hydroxyls.

Cell penetrating compounds, which include cationic import peptides (also called peptide translocation domains, membrane translocation peptides, arginine-rich motifs, cell-penetrating peptides, and peptoid molecular transporters), are capable of crossing biological membranes, i.e. lipid bilayers, and provide for assisted transport of a molecule to which they are linked through the membrane. In other words, they are capable of transporting molecules to which they are attached across membranes from one side of a lipid bilayer to the other side of the lipid bilayer, i.e. from outside a cell to inside a cell or from inside an endosomes to outside an endosome. Examples of cationic import peptides, which are typically rich in arginine and lysine, include TAT (SEQ ID 1), VP22 peptide, and an ANTp peptide (SEQ ID 2). Cell penetrating compounds, however, are not strictly peptides. Short, non-peptide polymers that are rich in amines or guanidinium groups are also capable of carrying molecules crossing biological membranes. Cationic import peptides are defined by their activity rather than by strict amino acid sequence requirements.

Another functional group comprises compounds, such as polyethylene glycol, that decrease interactions between molecules and themselves and with other molecules. Such groups are useful in limiting interactions such as between serum factors or cells and the molecule or complex to be delivered. These groups are referred to as steric stabilizers or interaction modifiers. A steric stabilizer is a long chain hydrophilic group that prevents aggregation by sterically hindering particle to particle electrostatic interactions. Examples include: PEG chains, poloxamers, and polysaccharides. An interaction modifier changes the way that a molecule interacts with itself or other molecules, relative to molecule containing no interaction modifier. For example, polyethylene glycol is an interaction modifier that decreases interactions between molecules and themselves and with other molecules.

Another functional group comprises alkyl chains and other hydrophobic groups such as cholesterol and cholesterol derivatives. These hydrophobic groups can be used to bind to membranes, disrupt membranes, or provide hydrophobic interactions.

A membrane permeable molecule is a molecule than can pass through a cell membrane bilayer. Movement of these molecules though the bilayer does not require additional proteins, compounds or chemicals. In fact, because of the impermeable nature of the cell membrane to charged or highly polar molecules, most small molecule drugs which need to reach the cell cytoplasm are membrane permeable. Drug design must often balance water solubility with membrane permeability. However, for certain drugs, such as the anticancer drug doxorubicin, non-specific membrane permeability leads to negative non-specific effects in non-target cells. The ability of reversibly inactivate the membrane permeable characteristics of such drugs could be used to improve efficacy of the drug while decreasing toxic effects.

A reactive group is a group that is able to form a covalent bond with another group. Reactive groups that form covalent bonds may be selected from the group comprising: isothiocyanate, isocyanate, acyl azide, acid halide, O-acyl urea, N-hydroxysuccinimide esters, succinimide esters, thioesters, amide, urea, sulfonyl chloride, aldehyde, ketone, ether, epoxide, carbonate, alkyl halide, imidoester, carboxylate, alkylphosphate, arylhalides (e.g. difluoro-dinitrobenzene), and anhydrides.

R groups comprise any group that one may desire to attach to the maleic anhydride. R groups may be selected from the group that comprises: peptides, proteins, antigens, haptens, biotin, nucleic acids, alkyl groups, etc.

Figure 3:
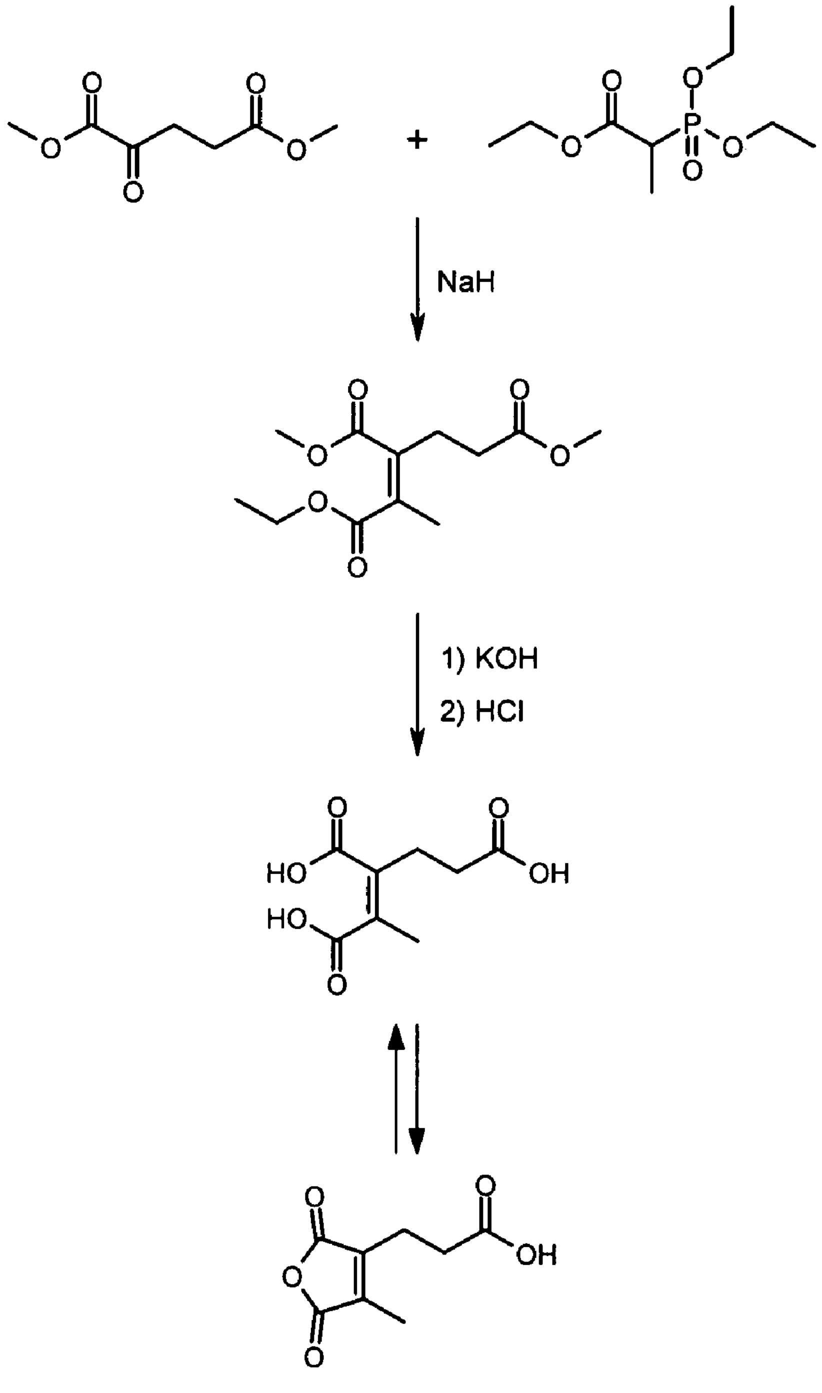
FIG. 3. Illustration of the steps in the synthesis of carboxy dimethylmaleic anhydride.
Figure 4:
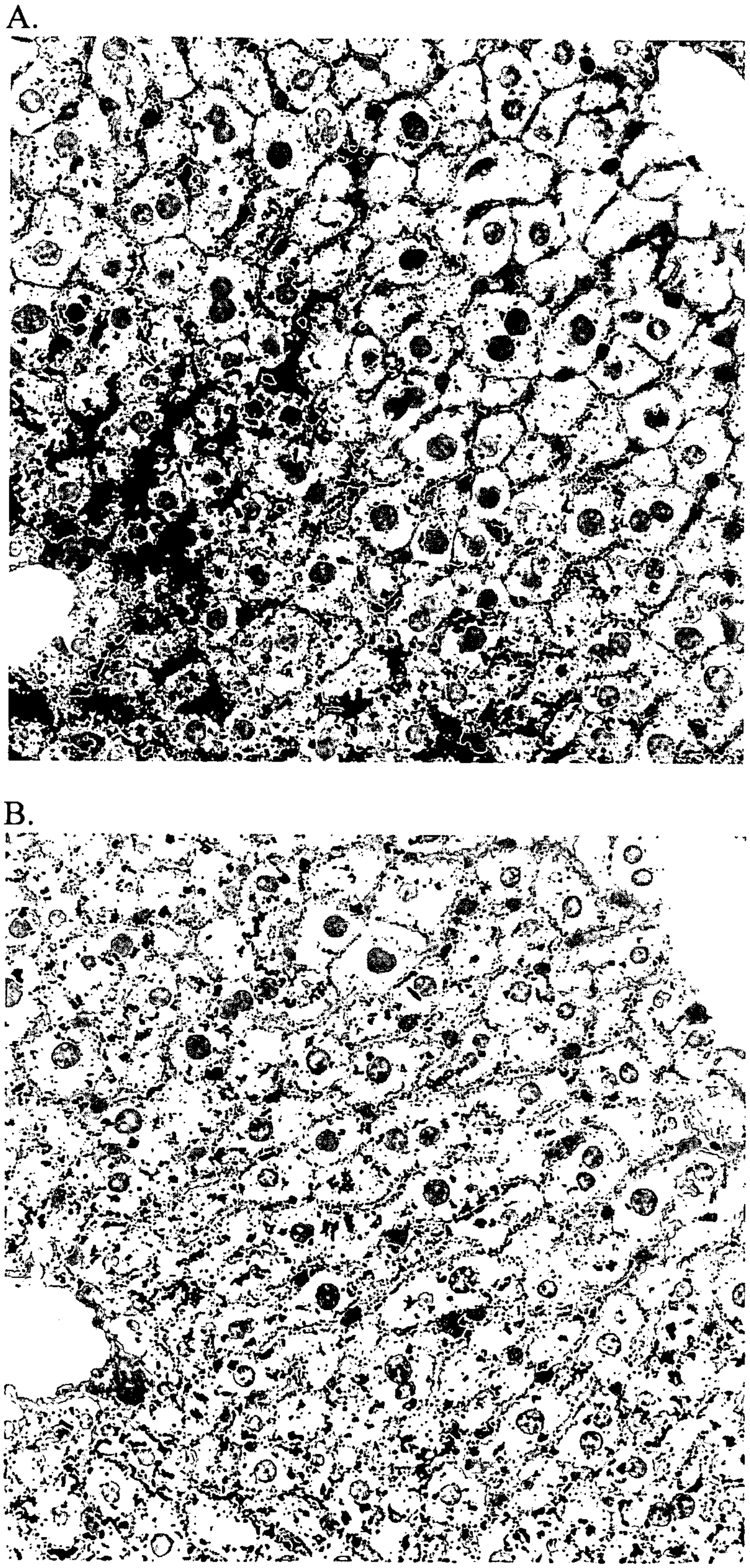
FIG. 4. Delivery of a Streptavidin to hepatocytes in vivo. Streptavidin was linked to a hepatocyte-targeting peptide and to the TAT cell penetrating peptide. The cell penetrating peptide was either unmodified (A) and reversible inactivated by modification with CDM (B). When the highly cationic TAT peptide was reversibly inactivated by CDM modification, a broader more even distribution of streptavidin was observed.

CDM (2-propionic-3-methylmaleic anhydride). CDM is a carboxylic acid-containing derivative of the disubstituted dimethylmaleic anhydride. CDM is synthesized via a Horner-Emmons reaction between dimethyloxoglutarate and triethyl-2-phosphonopropionate followed by saponification of the ester groups according to the published procedure (FIG. 3) (Naganawa et al. 1994). The addition of a carboxylate-containing group increases charge and water solubility of the compound. The cis-aconitic anhydride has a similar carboxylic acid group but lacks the disubstitution at second R position.

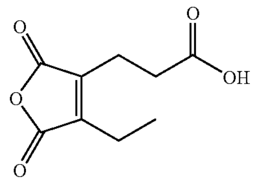

Ethyl CDM-(2-propionic-3-ethylmaleic anhydride)

Phosphorodiamidate morpholino oligonucleotides (PMOs). PMOs are assembled from morpholino subunits, each of which contains one of the genetic bases linked to a 6-membered morpholine ring. The subunits are joined by non-ionic phosphorodiamidate intersubunit linkages. PMOs exert their effects by steric hindrance mechanisms and can be used to block translation or splicing of a target RNA. Like PEG and dextran, oligonucleotides are internalized by fluid phase endocytosis and are unable to diffuse directly across cell membranes.

Crosslinking refers to the attachment of two or more molecules with a bifunctional reagent (crosslinker). A bifunctional reagent is a molecule with two reactive ends. The reactive ends can be identical as in a homobifunctional molecule, or different as in a heterobifunctional molecule. The attachment can be a covalent bond or a stable non-covalent bond.

A labile bond is a covalent bond that is capable of being selectively broken. That is, the labile bond may be broken in the presence of other covalent bonds without the breakage of other covalent bonds. For example, a disulfide bond is capable of being broken in the presence of thiols without cleavage of any other bonds, such as carbon-carbon, carbon-oxygen, carbon-sulfur, carbon-nitrogen bonds, which may also be present in the molecule. Labile also means cleavable.

A labile linkage is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative.

pH-labile refers to the selective breakage of a covalent bond under acidic conditions (pH<7). That is, the pH-labile bond may be broken under acidic conditions without the breakage of other covalent bonds. The term pH-labile includes both linkages and bonds that are pH-labile, very pH-labile, and extremely pH-labile.

A subset of pH-labile bonds is very pH-labile. For the purposes of the present invention, a bond is considered very pH-labile if the half-life for cleavage at pH 5 is less than 45 minutes.

A subset of pH-labile bonds is extremely pH-labile. For the purposes of the present invention, a bond is considered extremely pH-labile if the half-life for cleavage at pH 5 is less than 15 minutes.

A molecule is modified, to form a modification through a process called modification, by a second molecule if the two become bonded through a covalent bond. That is, the two molecules form a covalent bond between an atom from one molecule and an atom from the second molecule resulting in the formation of a new single molecule. A chemical covalent bond is an interaction, bond, between two atoms in which there is a sharing of electron density.

Native chemical ligation is the formation of an amide bond between the carboxylate of thioester and the amine of a compound that also contains a thiol two or three atoms away from the amine, such as a terminal cysteine.

Charge, Polarity, and Sign. The charge, polarity, or sign of a compound refers to whether or not a compound has lost one or more electrons (positive charge, polarity, or sign) or gained one or more electrons (negative charge, polarity, or sign).

Application Ser. Nos. 10/444,662, 09/589,978 and 11/045, 590 are incorporated herein by reference.

EXAMPLES

1. Synthesis of 2-carboxyethyl-3-methyl-maleic anhydride (CDM-thioester). CDM anhydride (100 mg) was dissolved in 10 mL methylenechioride. To this solution was added 2 mL oxalyl chloride. After stirring overnight, excess oxalyl chloride was removed by rotary evaporation to yield a clear oil. The acid chloride of CDM was then dissolved in 10 mL methylenechloride. To this solution was added 200 mg mercaptoacetic acid and 100 µL diisopropylethylamine. The solution was stirred for 1 h and the solvent was removed by rotary evaporation. The resulting oil was placed under high vacuum (0.2 torr) for 3 h to remove excess mercaptoacetic acid and diisopropylethylamine. The product was dissolved in water and acetonitrile (9:1) and purified by HPLC using a reverse-phase C18 column loading in water:acetonitrile (9:1 with 0.1% trifluoroacetic acid) and eluting with acetonitrile (0.1% trifluoroacetic acid).

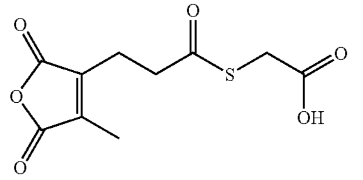

CDM-thioester

Other disubstituted maleic anhydride-base crosslinkers can also be made, including, but not limited to:

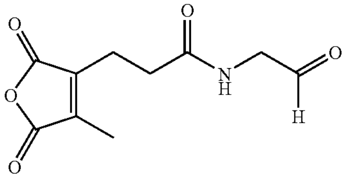

CDM aldehyde

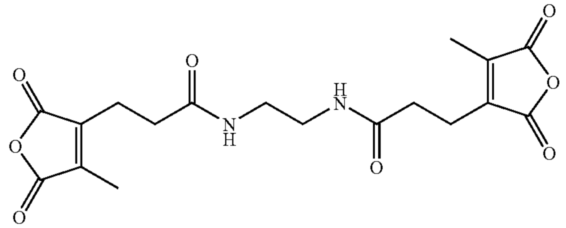

CDM-dimer

2. Charge reversal of a polyamine by modification with disubstituted maleic anhydrides. Cyclic anhydrides were reacted with the polyamine poly-L-lysine (PLL). To a solution containing 200 µg PLL, 2 mg HEPES, and 0.4 mg NaOH in 100 µL water was added 0.4 mg CDM or dimethylmaleic anhydride (Aldrich) in 50 µL ethanol with rapid vortexing. For cis-aconitic anhydride (Aldrich), 1 mg of anhydride, 5 mg of HEPES, and 1 mg of NaOH were used. Similarly, PLL was reacted with two equivalents of succinic or citraconic anhydride (Aldrich). Following reaction of PLL with the anhydrides, trinitrobenzenesulfonic acid (TNBS) assay indicated complete conversion of the ε-amines of PLL to carboxylates. The charge density of these polyanions was then determined by assessing their ability to condense cationic, fluorescein-labeled PLL. At neutral pH, one functional equivalent of succinylated PLL is required to condense PLL. Similarly, one equivalent of citraconylated PLL and one half equivalent of cis-aconitylated PLL (which has two carboxylate groups per repeating unit) are required to condense PLL. In contrast, PLL modified with dimethylmaleic anhydride is unable to condense PLL, even when 10 equivalents are added. Similarly, the charge density of CDM-modified PLL is one charge per two carboxylates. The distal carboxylate of the anhydride adds charge to the modified polymer while the carboxylate of the anhydride appears to contribute no charge to the polyanion.

3. Acylation of the dipeptide glycinylalanine and the kinetics of cleavage. The rates of acid-catalyzed cleavage of the maleamates were evaluated using the dipeptide glycinylalanine. CDM and dimethyl maleamic modified glycinylalanine (GA) were synthesized by addition of 400 µg CDM or dimethylmaleic anhydride in 20 µL ethanol to a solution of 200 µg GA and 2.4 mg HEPES base in 44 µL water. Cleavage was allowed to proceed by addition of the modified peptides to a pH 5 solution. At various times, 10 µg aliquots were removed and added to 0.5 mL of a 100 mM $NaHCO_3$ solution (pH9) containing 0.4 mM TNBS (pH9). The disubstituted maleamic acids cleaved much more rapidly than monosubstituted maleamic acids. A plot of ln $[1-(A_t/A_0)]$ as a function of time was a straight line whose slope is −k, the rate constant for the cleavage reaction, where $A_t$ is the absorbance at time t and $A_0$ is the absorbance of unmodified GA. The rate constants for the cleavage of dimethylmaleamic acid and CDM modified glycinylalanine were 0.4/min ($t_{1/2}$=1.5 min) and 0.3/min ($t_{1/2}$=2 min), respectively. Similar analysis for the reversal of cis-aconitic modification revealed much slower cleavage kinetics with an approximate half-life of 300 min (5 h).

| compound | half-life (minutes) |
|---|---|
| DM | 1.5 |
| CDM | 2.0 |
| cis-aconitic | 300 |

4. Reversible inactivation of a membrane active peptide modification with a disubstituted maleic anhydride. Little honey bee Melittin (SEQ ID 4) was acylated at pH 7.5 with two molar equivalents, relative to the four lysine residues, with succinic, cis-aconitic, dimethylmaleic, citraconic, and CDM anhydrides. To a solution containing 200 μg melittin, 500 μg HEPES, and 100 μg NaOH in 20 μL water was added 0.1 μg CDM or dimethylmaleic anhydride in 50 μL ethanol with rapid vortexing. For cis-aconitic anhydride 250 μg anhydride, 1.25 mg of HEPES, and 250 mg of NaOH were used. Measurement of amine content by TNBS revealed complete acylation of melittin by all of the anhydrides.

The membrane activity of the modified peptides was measured using a red blood cell (RBC) hemolysis assay. Porcine whole blood was isolated in heparin-containing vacutainers. RBC's were isolated by centrifugation at 2,500 rpm for 5 min and washed three times with 100 mM phosphate buffer. 20 μL of the washed RBC suspension (~$10^8$ cells) was added to 500 μL phosphate buffer. To this solution was added various amounts of peptide and the samples were incubated for 1.5 h at 37° C. Samples were then centrifuged for 1 min at 14,000 rpm. Lysis of the RBCs was determined by measuring the absorbance of the supernatant at 541 nm. Modification by all of the anhydrides except dimethylmaleic anhydride resulted in a complete loss of membrane activity.

Melittin modified with either CDM or cis-aconitic anhydride was incubated at pH 5. At various times, the pH was raised by the addition of pH 7.5 buffer and the hemolytic activity of each sample was measured. The membrane activity for CDM-melittin returned to 100% within 25 minutes. Kinetics of the return of activity (plotting of $\ln[1-(A_t/A_0)]$ revealed a rate constant of 0.07/min ($t_{1/2}$=10 minutes). Incubation of cis-aconitylated melittin at pH 5 for 27 h resulted in only a 30% return in activity. Analysis of the kinetics of its cleavage revealed a rate constant of 0.015/hr ($t_{1/2}$=47 hours). These results indicate that CDM is able to inhibit activity of a membrane active peptide. Furthermore, the inhibition is reversed at a physiologically relevant pH in timeframe amenable to delivery of material to cells via endocytosis.

5. CDM-Melittin mediated release of fluorescent polyethylene glycol from the endocytic compartment. HeLa cells grown on glass coverslips were incubated with 1 mg/ml fluorescein-PEG3000 either with or without 400 μg/ml modified melittin in 1 ml DMEM for 10 min at 37° C. After this pulse, cells were washed and chased for an additional 35 min at 37° C. in DMEM+10% bovine serum. Cells were then washed three times with PBS (Sigma), fixed for 30 min in PBS+4% formaldehyde (Sigma) at 4° C., and washed three times in PBS. Coverslips were then mounted onto glass slides for fluorescent microscopy. Images of the samples were collected by confocal microscopy on a Zeiss LSM510 confocal microscope (Zeiss, Germany). In the absence of CDM-melittin, the fluorescein-PEG had a punctuate appearance, indicative of localization in endosomes and/or lysosomes. In contrast, when CDM-melittin was included diffuse fluorescence was observed throughout the cell, indicating release of fluorescein-PEG from internal endosomes/lysosomes. Co-incubation with cis-aconitic modified melittin resulted in punctate fluorescence indistinguishable from fluorescein-PEG alone control. Similar results were observed when fluorescein-labeled 10 kDa dextran was used as the marker molecule. In addition, bafilomycin, an inhibitor of endosomal acidification, inhibited release of the fluorescein-PEG.

Incubation of cells with 400 μg/ml CDM-melittin for 10 min had no visually apparent cytotoxic effect. In contrast, 10 μg/ml unmodified melittin completely destroyed cells in less than 10 minutes. Additionally, propidium iodide staining was used to provide a more sensitive indication of cellular toxicity. In the cells exposed to CDM-melittin for 10 min, only ~1% of cells subsequently showed nuclear staining with propidium iodide, similar to control samples. Thus, CDM-melittin enabled endosomal release while substantially reducing its cellular toxicity.

6. Cytoplasmic/nuclear delivery of an oligonucleotide with CDM-modified membrane active peptide. HeLa-LUC/705 cells carry a stably integrated mutant luciferase gene that has a defective splice site (Gene-Tools, Philomath, Oreg.). This mutant splice site results in production of a mRNA coding for a truncated, inactive luciferase protein. The presence of an appropriate phosphorodiamidate morpholino oligonucleotide (PMO, sequence CCT CTT ACC TCA GTT ACA ATT TAT A, SEQ ID 6) blocks this splice site leading to correct splicing and expression of the full-length active enzyme. Therefore, luciferase activity in this cell line is directly proportional to the amount of PMO present in the cytoplasm/nucleus (released from the endosomal compartment).

HeLa-LUC cells were incubated with 2.5 μM PMO±2.5 nM CDM-melittin, citraconyl-melittin, or aconityl-melittin. Cells were incubated for 4 hours in a humidified, 5% $Co_2$ incubator at 37° C. The media was then replaced with DMEM containing 10% fetal bovine serum and cells were incubated for an additional 48 h. The cells were harvested and lysates were then assayed for luciferase expression using a Lumat LB 9507 (EG&G Berthold, Bad-Wildbad, Germany) luminometer. Co-incubation of PMO with CDM-melittin resulted in 5-12 fold increase in luciferase expression above incubation with PMO alone. Neither cis-aconitic-modified melittin nor citraconic-modified melittin resulted in any increase in luciferase expression/PMO delivery.

| Condition | Luciferase Induction |
|---|---|
| PMO alone | 1.0 |
| + CDM-melittin | 8.5 ± 3.0 |
| + citraconyl-melittin | 1.2 ± 0.3 |
| + aconityl-melittin | 1.2 ± 0.4 |

These data indicate that CDM-melittin, but not citraconyl-melittin or aconityl-melittin regains activity on a time scale that enables delivery of oligonucleotides to cells.

7. Reversible attachment of an oligonucleotide to a polymer. In order to deliver a biologically active molecule to a cell in vivo, the reversibly-modified membrane active compound must be complexed with the molecule to be delivered. To link PMO's with CDM-modified melittin, we have developed coupling techniques based upon native chemical ligation in which a thioester and an N-terminal cysteine group react to form an amide bond. A benefit of this procedure is that the acid (of CDM) which is to be converted to an amide may be preactivated as a thioester. The thioester itself is relatively stable when compared to activated esters such as N-hydroxysuccinimidyl esters, but will couple readily and selectively with N-terminal cysteine groups. The reaction mixture may contain other amines and other thiols, but only an amino-terminal cysteine couples to form a stable amide (thiol within 2-3 bonds of an amine).

The stability of the thioester allows reaction of the anhydride of CDM-thioester with an amine on the PMO to form maleamic acid groups without reaction between amine and thioester. The resultant thioester is then able to react with an amino-terminal cysteine group that has been placed onto a polycation such as polyethyleneimine (PEI-Cys). In this way, we are able to attach the PMO to the polycation through the acid-labile maleamic group. Following the attachment of the PMO to PEI-Cys, CDM-thioester modified melittin is coupled to the PEI-Cys-PMO conjugate to form a single molecule complex that contains PEI-Cys, PMO, and CDM-modified melittin.

To synthesis cysteine-modified polyethyleneimine, $N_\alpha$-Fmoc-S-tert-butylthio-L-cysteine (20 mg) was dissolved in 5 mL of acetonitrile. To this solution was added dicyclohexylcarbodiimide (10 mg) and N-hydroxysuccinimide (5 mg). The succinimidyl ester was allowed to form overnight. The reacted dicyclohexylurea was then filtered off and the ester was added to a solution of polyethyleneimine (20 mg) in 10 mL of methanol. After 10 min, the derivatized polymer was precipitated out of solution by addition of 45 mL diethylether. The polymer was then dissolved in 2 mL piperidine to remove the FMOC groups. The polymer was again precipitated out of solution by addition of diethylether. The modified polymer was dissolved in 2 mL water and the solution was adjusted to pH 4 by addition of hydrochloric acid.

8. Oligonucleotide-polycation complex delivery assay. 0.5 nmol amine-modified PMO (SEQ ID 6, Gene Tools, Philomath, Oreg.) was reacted with 1 nmol CDM-thioester in the presence of 500 mg HEPES buffer pH 7.9. The modified PMO was then added to a 50 μL solution containing 10 μg/mL PEI-Cys, 1 mM dithiothreitol, and 5 mM HEPES buffer pH 7.5. Melittin was modified with CDM-thioester by reaction with 0.5 wt equivalent CDM thioester in the presence of 3 wt equivalents HEPES base. After 1 h of conjugation, CDM-thioester modified melittin was added to the PEI-Cys-PMO complex to a final concentration of 80 μg/ml melittin. Similar conditions were used to attach either citraconyl-Melittin or aconityl-Melittin to PEI-Cys-PMO. HeLa Luc/705 cells were grown under conditions used for HeLa cells. The cells were plated in 24-well culture dishes at a density of $3\times10^6$ cells/well and incubated for 24 hours. Media was replaced with 0.5 ml DMEM and the PMO complexes were added. The cells were incubated for 4 hours in a humidified, 5% $CO_2$ incubator at 37° C. The media was then replaced with DMEM containing 10% fetal bovine serum. The cells were then incubated for an additional 48 h. The cells were then harvested and the lysates were then assayed for luciferase expression.

PEI-Cys-PMO-CDM-Melittin addition was effective in delivery of PMO, while PEI-Cys-PMO-citraconyl-melittin and PEI-Cys-PMO-aconityl-melittin additions were not.

| Condition | Luciferase Induction |
|---|---|
| PMO alone | 1 |
| PEI-Cys-PMO-CDM-melittin | 67 |

9. Reversible inhibition of a cell penetrating compound. The cationic import peptide cysteine-TAT (CGRKKRRQRRR,SEQ ID 7) was labeled with the fluorophore Texas Red. This modification does not affect the import properties of the peptide and provides a visual assay for internalization. To a solution of 1 mg cysteine-modified TAT (SEQ ID 7) (10 mg/mL) and 10 mM HEPES buffer pH 7.5 was added 0.2 mg of Texas Red C5 bromoacetamide (Molecular Probes) in 500

μL of ethanol. After reacting overnight at room temperature, the ethanol was removed by speed evaporation to yield the labeled peptide.

The labeled peptide was then acylated with the disubstituted maleic anhydrides, dimethylmaleic and CDM. TAT-Texas Red (50 μg, 10 mg/mL) was modified by addition of dimethylmaleic or CDM anhydrides (50 μg, 20 mg/mL in ethanol) in the presence of 100 mM HEPES buffer pH 7.9.

For analysis of TAT-mediated delivery, HeLa cells were plated in 6-well plates containing glass coverslips at a density of 50,000-100,000 cells per well. After 24-48 hours, when cells reached 40-75% confluency, growth media was aspirated off and replaced with 1.0 ml DMEM, either pre-cooled to 4° C. or pre-warmed to 37° C. TAT conjugates were then added and cells were incubated at either 4° C. or 37° C. At 4° C. endocytosis was completely blocked and the TAT-conjugates entered the cell only directly through the plasma membrane. At 37° C., endocytic internalization was also possible. After incubation at the indicated temperature for 1-2 hours, cells were washed three times with PBS, fixed for 30 min at 4° C. in PBS containing 4% formaldehyde, and again washed three times with PBS. Coverslips were then mounted onto slides for viewing in a Zeiss LSM510 confocal microscope. For fluorescein labeled conjugates, a 488 nm wavelength argon laser was used for excitation and a long pass 505 filter was used for detection. For rhodamine or Texas red conjugates, a 543 nm wavelength HeNe laser was used for excitation and a long pass 585 filter was used for detection.

Addition of the modified peptides to cells at 4° C. resulted in no transport of the peptide. The unmodified peptide showed intense intracellular localization under these conditions. Upon shift to 37° C., dimethylmaleamate-modified TAT regained its activity at while the CDM-modified peptide did not. Presumably, dimethylmaleamate-modified TAT was internalized into the acidic environment of the endosome at 37° C. Once in this acidic environment the anhydride was cleaved, restoring activity to the TAT peptide. In contrast, the CDM-modified TAT was not significantly endocytosed at 37° C., and therefore did not experience an acidic environment. The ability to regain transport activity thus appears to be dependent upon endocytosis into an acidic environment and cleavage of the dimethylmaleamate group to regenerate the active TAT peptide.

10. Reversible attachment of PEG using CDM. We have demonstrated the facile synthesis of CDM and CDM-thioester. The ease with which CDM and its derivatives may be synthesized enables us to easily make other acid cleavable materials. In particular, polyethyleneglycol (PEG) may be conjugated to CDM via the acid chloride of CDM. To a solution of 2-propionic-3-methylmaleic anhydride (30 mg, 0.16 mmol) in 5 mL methylene chloride was added oxalyl chloride (200 mg, 10 eq) and dimethylformamide (1 μL). The reaction was allowed to proceed overnight at which time the excess oxalyl chloride and methylene chloride were removed by rotary evaporation to yield the acid chloride, a clear oil. The acid chloride was dissolved in 1 mL of methylene chloride. To this solution was added polyethyleneglycol monomethyl ether, molecular weight average of 5,000 (815 mg, 1 eq) and pyridine (20 μl, 1.5 eq) in 10 mL of methylene chloride. The solution was then stirred overnight. The solvent was then removed and the resulting solid was dissolved in 8.15 mL water. In contrast, Garman and Kalindjian made a PEG-containing maleic anhydride using 2-bromomethyl-3-methylmaleic anhydride (Garman and Kalindjian 1987). Attempts in our lab to duplicate this synthesis were unsuccessful and it has been reported that this intermediate is "difficult to prepare in good yield and high purity" (Greenwald et al. 2000). The difficulty in synthesis makes the contribution of CDM to the synthesis of acid cleavable PEG derivatives nontrivial. Plasmid DNA labeled with Cy3 Label 1T(Mirus Corporation, Madison, Wis.) was compacted into a particle with a 1.2 fold charge excess of poly-L-lysine (mw:52,000). The particles were then reacted with either a non-reactive Polyethylene Glycol (mw: 5000) or with amine-reactive CDM-PEG at a 0.5 molar equivalent to amines on the poly-L-lysine. Particles, containing 50 μg DNA, were injected into the tail vein of ~20 gram male ICR mice. Blood was taken at one hour and the smears were inspected for Cy3 fluorescence still in circulation. The animals were then sacrificed and the liver, lung, kidney and spleen were harvested and snap frozen for cryosectioning and the resulting slices were inspected for Cy3 fluorescence. It was found that the PEG-CDM modification increased circulation times dramatically over unmodified PLL-DNA particles. The animal injected with the fluorescent particles treated with non-reactive Polyethylene Glycol showed no fluorescence in circulation in the blood at one hour and very little fluorescence in the liver, kidney or spleen, leaving the significant portion of fluorescence in the lung. The animal injected with the fluorescent particles treated with CDM-PEG showed a high level of fluorescence still in circulation in the blood at one hour and also had a high level of fluorescence evenly spread throughout the liver, kidney and spleen, with little fluorescence in the lung.

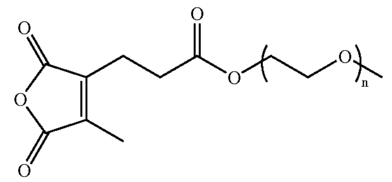

CDM-PEG n = integer greater than 0

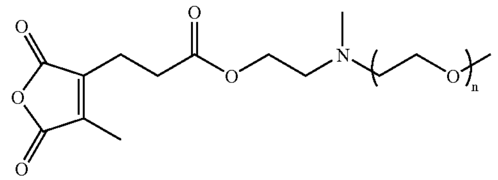

CDM-amine-peg

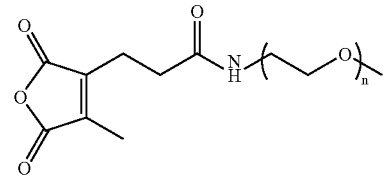

CDM-PEG amide, n = integer greater than 0

Using similar methods, other steric stabilizes or interaction modifiers can also be attached to a disubstituted maleic anhydride.

11. Reversible Modification of anticancer drug doxorubicin. To a 1 mM solution of doxorubicin (Dox) in 50 mM HEPES buffer pH 7.9 is added 3 equivalents CDM adduct (such as CDM or a CDM-polymer conjugate i.e. PEG-CDM). The modified DOX is then added to cells in tissue culture or injected in vivo.

12. Reversible Inhibition of a Membrane Permeable Peptide for Targeted Delivery: Streptavidin was modified with maleimide groups by reaction with 6 molar equivalents of Succinimidyl 4-[N-maleimidomethyl]cyclohexane-1-carboxylate (SMCC from Pierce). The liver targeting peptide Cys-PEG4-KNESSTNATNTKQWRDETKG-FRDEAKRFKNTAG (SEQ ID 8) was conjugated to streptavidin by reaction with the maleimide groups. 70,000 MW amino dextran with 18 amine groups/dextran (Molecular Probes) was reacted with 5 molar equivalents of Cy3 NHS ester (Amersham). The Cy3-labeled dextran was then reacted with 5 equivalents of NHS-activated biotin. The Cy3 and biotin labeled dextran was then reacted with 20 molar equivalents of SMCC. The Cy3/biotin/SMCC-modified dextran was isolated by size exclusion chromatography using sephadex G25. Cys-TAT peptide (prepared as described above) was then conjugated to the dextran via maleimide-thiol coupling and the dextran was isolated by size exclusion chromatography. 45 μg of Cy3/biotin/TAT-dextran was reacted with 80 μg of CDM in the presence of 4 mg HEPES base.

Unmodified and CDM-modified Cy3/biotin/TAT-dextran (45 μg) was added to 36 μg of liver-targeting peptide-streptavidin in 250 μL of PBS. These samples were injected into the tail vein of mice. 10 minutes postinjection, the mice were sacrificed, their livers harvested, frozen and sectioned for microscopy. A broader, more even distribution of labeled dextran was observed in the liver when the TAT cell permeable peptide was reversibly modified with CDM.

In a similar manner, a toxin, such as diphtheria toxin, or an anticancer drug can be conjugated to a cell permeable molecule such as the TAT peptide (SEQ ID 1). Inactivation of the TAT peptide by modification with CDM would prevent nonspecific toxicity. Activation of the TAT in the reduced pH environment of a tumor would lead to entry of the toxin into the cancer cells.

13. Reversible attachment of a targeting group: We have shown combining reactive groups and interaction modifiers to disubstituted maleic anhydrides for reversible modification of amine-containing compounds. It is also possible to create disubstituted maleic anhydrides with targeting groups for reversible attachment of the targeting groups to a compound. Examples of galactose-containing targeting groups on disubstituted maleic anhydrides include, but are not limited to:

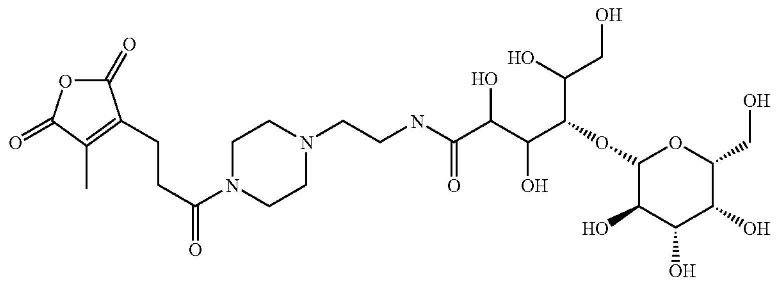

CDM-amine-lactobionic acid

-continued
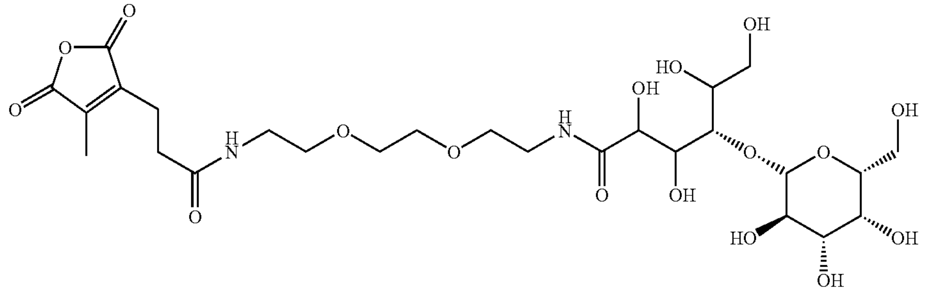
CDM-lactobionic acid
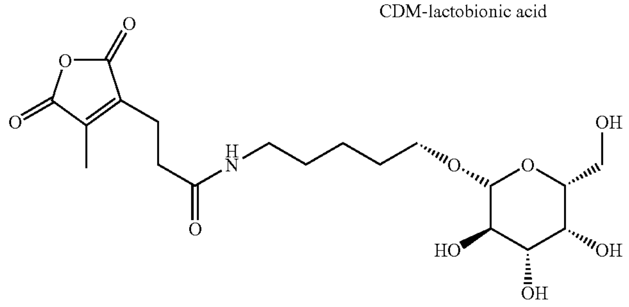
CDM-galactose
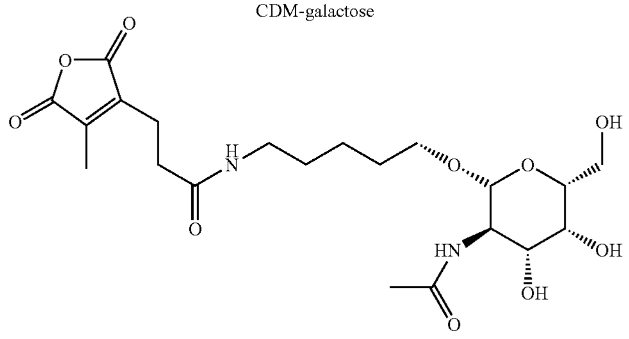
CDM-N-actyl galactose amine
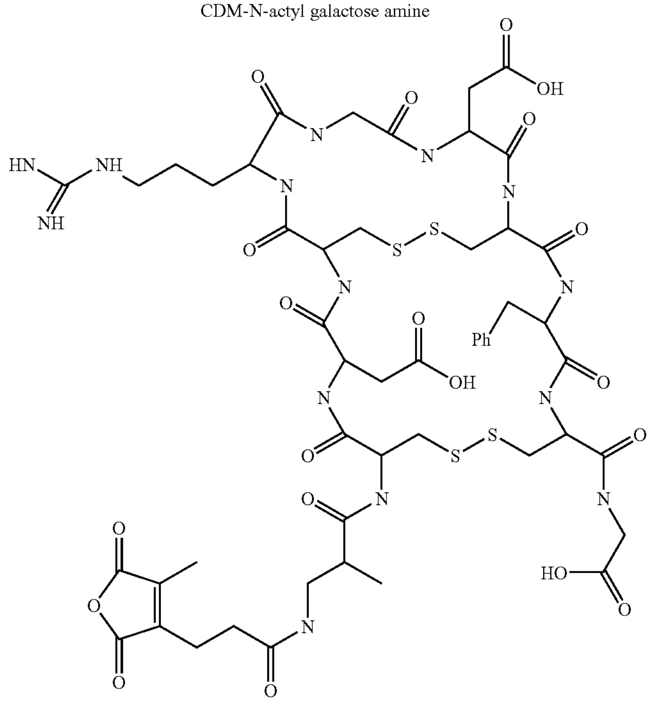
CDM RGD peptide (ACDCRGDCFCG, SEQ ID 9)

-continued

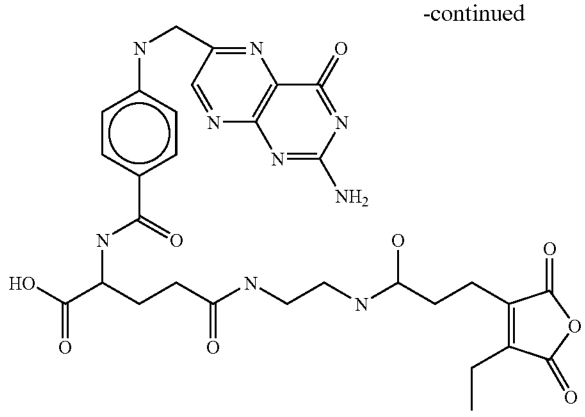

Ethyl CDM-folate

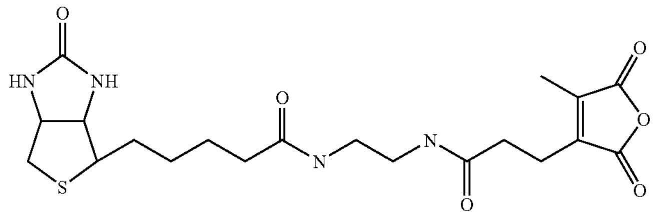

CDM-biotin

Those skilled in the art will readily recognize that targeting groups other than saccharides can readily be used.

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A process for reversibly modifying an amine-containing polycation polymer comprising: covalently attaching a disubstituted maleic anhydride containing a ligand for a cell surface receptor to an amine on the polycation polymer.

2. The process of claim 1 wherein the ligand is selected from the group consisting of: peptide, saccharide, galactose, and vitamin.

3. The process of claim 2 wherein the saccharide contains a terminal galactose or N-acetyl galactosamine.

4. The process of claim 2 wherein the peptide contains an arginine-glycine-aspartate sequence.

5. The process of claim 2 wherein the vitamin is selected from the group consisting of biotin and folate.

6. The process of claim 1 wherein attaching the maleic anhydride to the compound alters activity of the compound and cleavage of the maleic anhydride restores activity of the compound.

7. The process of claim 1 wherein the polycation polymer is associated via electrostatic or covalent interaction with a polynucleotide prior to covalent attachment of the disubstituted maleic anhydride.

8. A process for reversibly modifying an amine-containing compound comprising: covalently attaching a disubstituted maleic anhydride containing a hydrophilic steric stabilizer to an amine on the compound.

9. The process of claim 8 wherein the hydrophilic steric stabilizer is selected from the group consisting of: polyethylene glycol, poloxamer, saccharide, and polysaccharide.

10. The process of claim 9 wherein reversibly modifying an amine-containing compound reduces interaction of the compound with mammalian serum.

11. The process of claim 9 wherein the amine-containing compound consists of a cationic polyamine.

12. The process of claim 11 wherein the cationic polyamine is associated via electrostatic or covalent interaction with a polynucleotide prior to covalent attachment of the disubstituted maleic anhydride.

13. A process for reversibly modifying an amine-containing compound comprising: covalently attaching a disubstituted maleic anhydride containing a ligand for a cell surface receptor to an amine on the compound.

14. The process of claim 13 wherein the ligand is selected from the group consisting of: peptide, saccharide, galactose, and vitamin.

15. The process of claim 14 wherein the saccharide contains a terminal galactose or N-acetyl galactosamine.

16. The process of claim 14 wherein the peptide contains an arginine-glycine-aspartate sequence.

17. The process of claim 14 wherein the vitamin is selected from the group consisting of biotin and folate.

18. The process of claim 13 wherein attaching the maleic anhydride to the compound alters activity of the compound and cleavage of the maleic anhydride restores activity of the compound.

19. The process of claim 13 wherein the amine-containing compound consists of a polycation polymer.

20. The process of claim 13 wherein the polycation polymer is associated via electrostatic or covalent interaction with a polynucleotide prior to covalent attachment of the disubstituted maleic anhydride.

* * * * *